United States Patent [19]

Heaslip et al.

[11] Patent Number: 5,633,462

[45] Date of Patent: May 27, 1997

[54] METHOD AND APPARATUS FOR DETECTING THE CONDITION OF THE FLOW OF LIQUID METAL IN AND FROM A TEEMING VESSEL

[75] Inventors: Lawrence J. Heaslip, Scarborough; James D. Dorricott, Burlington, both of Canada

[73] Assignee: APA Systems, Lansing, Ill.

[21] Appl. No.: 277,409

[22] Filed: Jul. 19, 1994

[51] Int. Cl.$^6$ .................................................. G01H 11/00
[52] U.S. Cl. .......................... 73/649; 164/155.1; 164/453; 164/150.1; 73/1.83
[58] Field of Search ........................... 73/64.53, 53.01, 73/1 DV, 649, 658, 659; 164/155.1, 453, 457, 150.1, 4.1; 364/509, 508, 571.04

[56] References Cited

U.S. PATENT DOCUMENTS

| | | | |
|---|---|---|---|
| 2,865,196 | 12/1958 | Bordenave et al. | 73/597 |
| 3,435,664 | 4/1969 | Harris | 73/54.41 |
| 3,548,640 | 12/1970 | Deason et al. | 73/590 |
| 3,623,357 | 11/1971 | Abbotts | 73/32 R |
| 3,641,550 | 2/1972 | Lynas et al. | 73/583 |
| 3,654,072 | 4/1972 | Massa | 73/61.75 |
| 3,875,989 | 4/1975 | Pirlet | 164/4.1 |
| 3,906,780 | 9/1975 | Baldwin | 73/67.75 |
| 4,140,300 | 2/1979 | Gruner et al. | 266/45 |
| 4,145,917 | 3/1979 | Brazhnikov et al. | 73/64.53 |
| 4,235,095 | 11/1980 | Liebermann | 73/19.03 |
| 4,240,287 | 12/1980 | Mast et al. | 73/61.75 |
| 4,538,451 | 9/1985 | Reichard | 73/61.75 |
| 4,563,895 | 1/1986 | Eckert | 73/61.75 |
| 4,565,088 | 1/1986 | Crambes | 73/61.49 |
| 4,607,520 | 8/1986 | Dam | 73/61.03 |
| 4,973,386 | 11/1990 | Callegari et al. | 201/1 |
| 5,022,266 | 6/1991 | Cody et al. | 73/579 |
| 5,028,033 | 7/1991 | Morioka et al. | 266/45 |
| 5,042,700 | 8/1991 | Ardell | 164/4.1 |
| 5,083,452 | 1/1992 | Hope | 73/61.49 |
| 5,203,909 | 4/1993 | Petrushka et al. | 75/375 |
| 5,251,469 | 10/1993 | Chan | 73/1 DV |

FOREIGN PATENT DOCUMENTS

| | | | |
|---|---|---|---|
| 132613 | 8/1977 | Germany . | |
| 58-13455 | 1/1983 | Japan | 164/453 |
| 58-13464 | 1/1983 | Japan | 164/453 |
| 6221448 | 7/1985 | Japan . | |
| 3017215 | 3/1989 | Japan . | |
| 3264146 | 3/1990 | Japan . | |
| 3184824 | 8/1991 | Japan | 164/150.1 |
| 60118652 | 8/1993 | Japan | 164/155.1 |
| 1488308 | 12/1986 | U.S.S.R. . | |

*Primary Examiner*—Christine K. Oda
*Attorney, Agent, or Firm*—Ostrolenk, Faber, Gerb & Soffen, LLP

[57] ABSTRACT

An apparatus for detecting the condition of the flow of liquid metal in or from a teeming vessel includes a sensor for detecting vibration caused by a flow of liquid metal in or from the teeming vessel and for outputting a sensor signal corresponding to an amount of vibration detected by the sensor. A signal processor receives the sensor signal and compares the sensor signal to a reference signal and outputs a comparison signal. A logic unit receives the comparison signal and outputs a status signal indicative of the condition of the flow of the liquid metal in or from the teeming vessel.

28 Claims, 4 Drawing Sheets

METHOD AND APPARATUS FOR DETECTING THE CONDITION OF THE FLOW OF LIQUID METAL IN AND FROM A TEEMING VESSEL

BACKGROUND OF THE INVENTION

1. Field of the Invention

The present invention relates to a method and apparatus for detecting the condition of the flow of liquid metal in or from a teeming vessel and more particularly to a method and apparatus for detecting the presence of an undesirable condition in the flow of liquid metal in or from the teeming vessel.

2. Description of the Prior Art

Liquid metal and in particular liquid steel is drained from a draining or teeming vessel, normally a ladle, into one or more molds usually through an intermediate or receiving vessel, normally a tundish. In this process, a controlled flow of liquid metal passes from the ladle, normally through a nozzle and valve in the bottom of the ladle, into a ceramic tube and then into a receiving vessel, normally a tundish. A tundish is a refractory-lined vessel equipped with one or multiple outlets through which the metal flows into the mold(s).

As the teeming ladle approaches empty, slag and oxidation products which float on-top of the liquid steel in the ladle, can be entrained within the teeming flow and transferred to the tundish. Usually, as the teeming ladle is approaching empty, the surface of the liquid steel in the tundish is observed visually and when slag is seen to be entering the receiving vessel, the valve in the teeming ladle is closed in order to reduce the contamination of the metal in the tundish or mold with slag and oxidation products. Alternatively, an electromagnetic coil may be employed to assist in the detection of the presence of slag or non-metallics in the teeming flow and to automatically signal for valve closure. Typically, this coil surrounds the nozzle of the teeming ladle and senses variations of the electromagnetic field produced by the excitation of the coil related to changes in non-metallic content of the flow.

It is well known that flow from a teeming ladle induces vibration of the ladle itself, the ceramic tube which is attached to the ladle, and the tundish. In particular, vibration of the tube can be substantial. Attempts have been made to sense this vibration manually.

The prior art does not address the following problems:
Visual Slag Detection

Visibility of slag entrainment within the tundish is poor. Therefore, the ability of the ladle teeming operator to see slag is difficult and the consistency of ladle flow closure is poor. Early ladle closure results in lost metal yield and late ladle closure results in slag contamination of the liquid steel in the tundish. As multiple ladles are poured into one tundish, slag build-up occurs and the problem of visibility is compounded. A significant problem associated with visual slag detection is that slag is not seen until it is already present in the tundish.

Electromagnetic Slag Detection

The sensor coil is located in the ladle and therefore, is highly susceptible to thermal and physical damage. The ladle must be specifically adapted to accept the coil and as each ladle arrives at the teeming position, a cable connection must be performed. Steel penetration in the nozzle block can damage the coil or impede its operation. A teeming ladle must be removed from the operational cycle to replace a damaged or non-performing coil. In this situation, slag is not detected until it is present within the nozzle block of the teeming ladle and already flowing toward the tundish.

Prior Art Vibration Sensing

Manual vibration sensing is inconsistent and operator dependent. The human threshold to sense and discriminate change in vibration is limited. As with the above two methodologies, slag is detected when it is present and flowing through the tube attached to the ladle.

SUMMARY OF THE INVENTION

Accordingly, it is an object of the present invention to provide a method and apparatus which utilizes vibra-acoustic signals to characterize and detect changes in the flow condition or behavior of liquid metal which presage the onset, or are characteristic of, slag entrainment within the metallic flow passing from a draining vessel.

Another object is to provide a logic which allows a means for flow discrimination and provides alarms which indicate a deviation between a desired flow condition of a ladle and undesired flow conditions such as vortexing, flow rate irregularity, surface collapse, flow plugging, slag entrainment, and gaseous aspiration.

It has been found that the above and other objects of the present invention are attained in an apparatus for detecting the condition of the flow of liquid metal in or from a teeming vessel including a sensor for detecting vibration caused by a flow of liquid metal in or from the teeming vessel and for outputting a sensor signal corresponding to an amount of vibration detected by the sensor. A signal processor receives the sensor signal and compares the sensor signal to a reference signal and outputs a comparison signal. A logic unit receives the comparison signal and outputs a status signal indicative of the condition of the flow of the liquid metal in or from the teeming vessel.

A method for detecting a condition of a liquid metal flow in or from a teeming vessel includes detecting an amount of vibration caused by the liquid metal flowing in or from the teeming vessel. The detected amount of vibration is converted to a sensor signal. The sensor signal is compared to a reference signal to output a comparison signal. A status signal is outputted in response to the comparison signal, the status signal being indicative of a condition of the flow of the liquid metal in or from the teeming vessel.

Other features and advantages of the present invention will become apparent from the following description of the invention which refers to the accompanying drawings.

BRIEF DESCRIPTION OF THE DRAWING(S)

For the purpose of illustrating the invention, there is shown in the drawings an embodiment which is presently preferred; it being understood, however, that the invention is not limited to the precise arrangements and instrumentalities shown.

DETAILED DESCRIPTION OF THE INVENTION

The present invention relates to a method and apparatus which discriminates vibration associated with liquid metal flow, slag or slag-contaminated liquid metal flow, and alterations in flow behavior or condition which presage the onset of slag entrainment within the metallic flow passing from a teeming or draining vessel such as a ladle.

Figure 1:
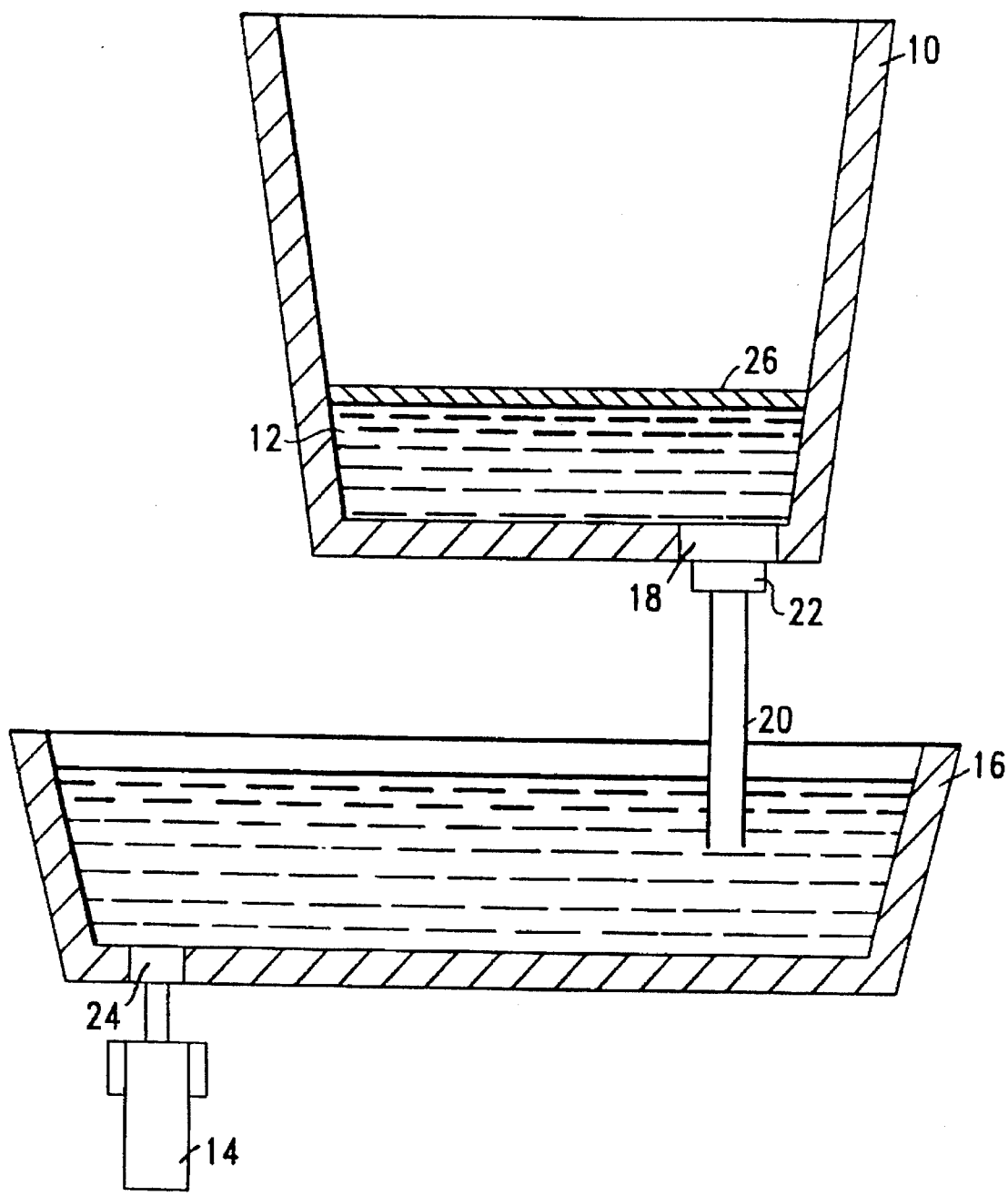
FIG. 1 is a typical arrangement in a steel making process showing apparatus used to pour liquid metal from a teeming vessel or ladle and ultimately into a mold.

Referring now to the drawings wherein like numerals indicate like elements, there is shown in FIG. 1 a general arrangement of apparatus typically used in a continuous casting steel making process in which the presence of contaminants in the flow of liquid metal is sought to be detected. In the continuous casting process, a draining vessel or ladle 10 is filled with liquid metal 12 and transfers the liquid metal 12 into one or more molds 14 through an intermediate or receiving vessel called a tundish 16. A controlled flow of the liquid metal 12 passes from the ladle 10 to the tundish 16 through a nozzle 18 located in the bottom of the ladle 10, and through a tube 20, preferably a ceramic tube. The nozzle 18 includes a valve 22 to control the rate of flow of the liquid metal 12 out of the ladle 10. The tundish 16 is equipped with one or more outlets 24 through which the liquid metal 12 flows into a corresponding (i.e. one or more) number of the molds 14.

When the ladle 10 contains little or no liquid metal 12, the ladle 10 is replaced with another ladle, not shown, filled with liquid metal 12 to insure that the liquid metal 12 flows continuously to the mold(s) 14. When the second ladle, not shown, similarly runs out of the liquid metal 12, it too is replaced with another ladle, not shown, filled with liquid metal 12. This is a continuous process.

A problem with continuous steel casting arises when the ladle 10 approaches empty. The presence of an impurity such as slag 26, which typically forms a layer on the liquid metal 12, becomes entrained in the liquid metal 12 passing through the valve 22 and the tube 20. This contaminates the liquid metal 12 passing into the tundish 16, and ultimately into the mold(s) 14. This is undesirable.

When the ladle 10 is filled with the liquid metal 12, the presence of the slag 26 or other impurities floating on top of the liquid metal 12 is far enough away from the nozzle 18, that the slag 26 does not become entrained with the liquid metal 12 passing from the ladle 10 to the tundish 16. The flow of the liquid metal 12 from the tundish 10 and through the nozzle 18 at that point is, therefore, an uncontaminated flow, or a substantially uncontaminated flow.

The method and apparatus of the present invention uses vibration sensing, analysis, and alarm logic for the discrimination of the flow of the liquid metal 12 from the ladle 10. This process provides alarms which indicate a deviation between the desired condition of the flow of the liquid metal from the ladle 10, and undesired flow conditions such as slag entrainment as the ladle 10 approaches empty. It is within the scope of the present invention to detect other undesirable flow conditions such as vortexing, flow rate irregularity, surface collapse, flow plugging, and gaseous aspiration.

Alarms are provided to indicate undesirable changes in flow condition. Alarms associated with vortexing, and/or flow rate irregularity, and/or surface collapse can presage the onset of slag flow or entrainment. The present invention can be used to aid the human operator in deciding to stop the flow by closing the valve 22. Alternatively, alarm logic can provide a signal to automatically or manually initiate closure of the valve 22.

Figure 2:
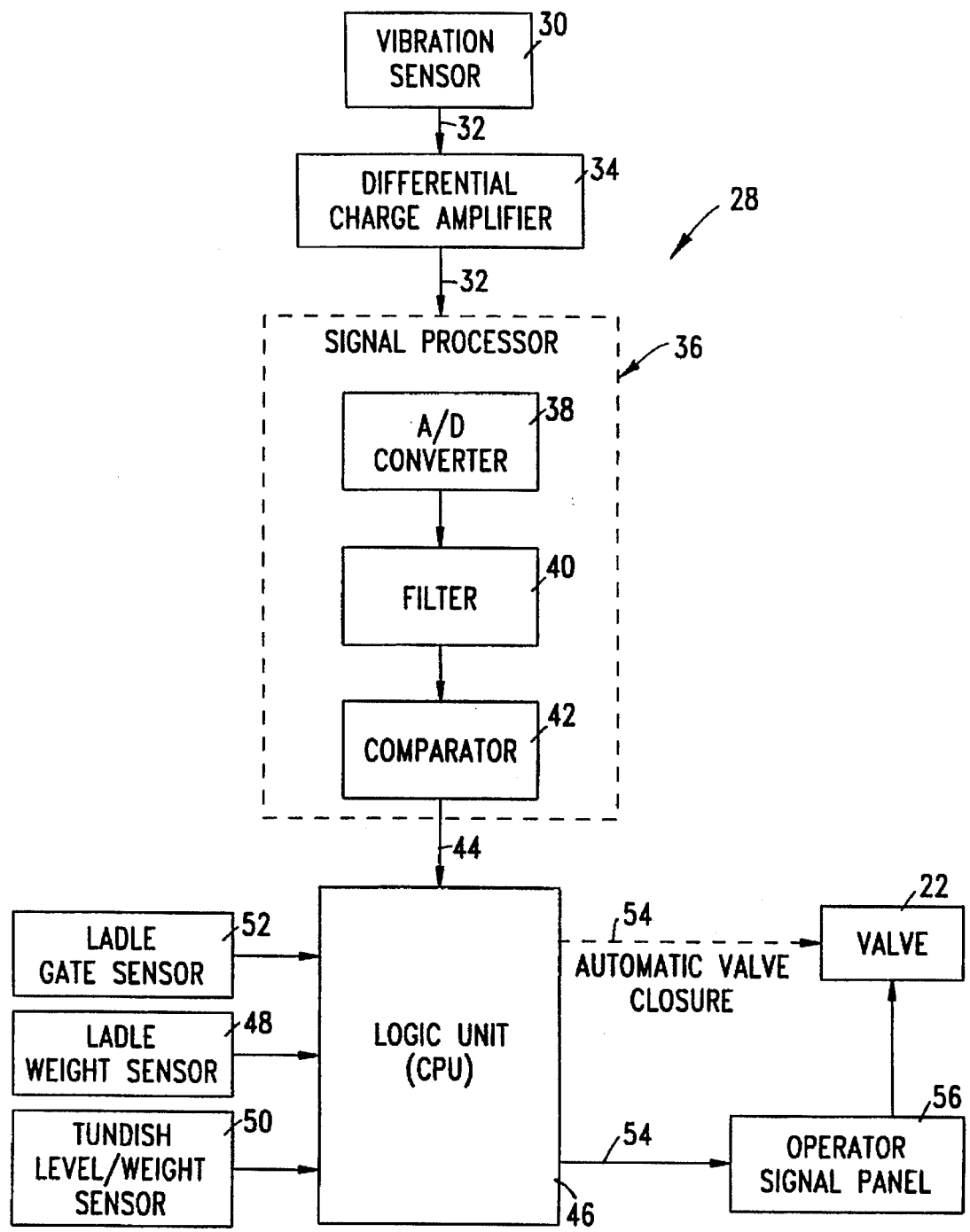
FIG. 2 is a schematic diagram showing the elements used to detect an undesirable flow condition in the flow of liquid metal in and from the teeming vessel or ladle of FIG. 1.

Referring now to FIG. 2, there is shown at 28 a general arrangement of the method and apparatus of the present invention for detecting the condition of the flow of the liquid metal 12 in and/or from the ladle 10. A vibration-sensing device or sensor 30 such as a microphone, or in a preferred embodiment a delta-shear type accelerometer, is used to sense the vibration induced by the flow of the liquid metal 12 in or from the ladle 10. The vibration sensor 30 outputs an analog electrical signal or sensor signal 32 which allows measurement of the vibration. The accelerometer can be obtained from any of the known suppliers including Brüel & Kjaer of Denmark or Hewlett Packard.

The sensor 30 may be coupled to the vibration source by any of the known methods, e.g. bolts or magnetic means. It is not required that the sensor 30 be in direct contact with the liquid metal flow channel. For example, the sensor 30 can be coupled directly to the ceramic tube 20 if the sensor 30 is able to withstand temperatures associated with the ceramic tube 20. In a preferred embodiment, the sensor 30 is coupled to a lifting device, not shown, which moves the tube 20 into and out of alignment with the ladle 10 and tundish 16. The sensor 30 can be coupled to the tube 20 or the lifting device, not shown, by a magnet. Alternatively, the sensor 30 can be bolted directly to the ceramic tube 20 or lifting device or any other elastic solid, i.e. a solid capable of passing vibration, which is in direct contact with the vibration source.

Once the vibration sensor 30 generates the sensor signal 32, it is passed to a differential charge amplifier 34 consisting of two high gain, low noise operational amplifiers. A filter network around the input amplifier provides a fall-off in response below 10 Hz. This eliminates the influence of low frequency noise from the sensor signal 32 which could be caused by the effects of fluctuating temperature. Preferably, the charge amplifier 34 has a balanced low-impedance output suitable for drawing, i.e. passing signals, through long cables. The charge amplifier can be obtained from any of the known suppliers, including the suppliers described above.

The sensor signal 32 from the charge amplifier 34 is passed to analysis electronics or an analysis unit 36 such as a signal processor for continuous analysis. The analysis or signal processing of the sensor signal 32 allows for the discrimination of the signal 32. In a preferred embodiment, the analysis/signal processing is performed by a real-time frequency analyzer which allows rapid frequency analysis and simultaneous spectral comparison such that no signal data is lost. The signal processor can be obtained from any of the known suppliers, including the suppliers described above.

Within the signal processor 36, the analog sensor signal 32 is first converted to a digital data signal by an analog to digital converter 38. In a preferred embodiment, the analog sensor signal 32 is converted to a digital data signal internally by a signal analyzer using a nine-pole elliptical low pass filter which supplies at least 84 dB of attenuation of high-frequency signals.

During and/or after conversion, the digital data signal is processed using constant-percentage bandwidth filters 40 to divide the digital data signal into those portions associated with various frequency bands over the frequency range of interest, e.g. a frequency range of 0.1 Hz to 20 kHz. This is referred to as frequency analysis. The output of the frequency analysis is a data spectrum.

The data spectrum is rapidly and continuously generated and compared to a calibration spectrum by a comparator 42. A calibration spectrum is generated for the desired flow condition (i.e. free of vortices, slag, contaminants, etc.). In the comparator 42, the data spectrum is continually laid over the calibration spectrum to determine when the intensity level of the data spectrum is outside a preprogrammed standard deviation which is an integral part of the calibration spectrum. This is referred to as spectral comparison.

The differences between the data spectrum and the calibration spectrum are calculated by the comparator 42 and yield spectral comparison data 44. The magnitudes of the spectral comparison data 44 are processed within a logic unit or central processing unit ("CPU") 46. In a preferred embodiment, the CPU 46 is a Compaq 486DX266 IBM compatible programmable computer, although it should be realized that other types and brands of CPU's are within the scope of the present invention, e.g. Apple computers, RISC based computers, Silicon Graphics work stations or the like.

The CPU 46 generates a status signal 54 such as a contaminant or flow condition change warning signal and/or a ladle shut-off signal using a logic based upon the magnitudes of the spectral comparison data 44. This logic is based upon the magnitude of the variance of the spectral comparison data 44 outside of about 88% to 95% confidence intervals. In other words, the difference between the real time generated data spectrum and the calibration spectrum is calculated at frequent intervals (typically on the order of 500–1000 milliseconds) and the logic assumes that variance in this difference larger than a specific confidence interval placed around the calibration spectrum, is indicative of the alterations of flow condition which can be characterized at different spectral frequencies or bands such as vortexing, surface collapsing, flow rate, gaseous aspiration and/or slag entrainment.

The CPU 46 contains adjustable limits of the confidence interval and the magnitude of the differences between the adjusted confidence interval and the measured spectral data, to allow the adjustment of the sensitivity of the system to the flow condition changes previously defined. In addition, the logic allows the independent adjustment of the confidence interval associated with individual frequencies or bands in order to allow the adjustment of the sensitivity of the system to the different flow conditions which are experienced.

The logic can simply involve the presence of a specific magnitude of the spectral comparison data 44 or can include a time history, and/or ladle weight factors to enhance alarm sensitivity. The CPU 46 can have as input, signals from steel making process equipment such as the ladle weight determined from a ladle weight sensor 48, the tundish level or weight determined from a tundish level/weight sensor 50, and/or the ladle gate or valve position determined from a ladle gate or valve position sensor 52. This allows the sensitivity of the logic to be varied as a function of ladle weight, and for the system to automatically control and close the ladle gate or valve 22. For example, as the ladle 10 gets closer and closer to empty, the likelihood of slag entrainment or a similar undesirable flow condition is increased and the sensitivity of the logic is increased accordingly.

The output from the CPU 46 is used to pass the status signal 54 to the operator signal panel 56 which indicates the state, e.g. an alarm state, of the flow condition. The status signal 54 can be used to aid the operator of the signal panel 56 in deciding whether to stop the flow of liquid metal by closing the valve 22. The status signals 54 may also be used to signal for, or automatically initiate closure of, the ladle valve 22.

In use, the method and apparatus 28 of the present invention is first used to determine the standard deviation for the calibration spectrum for the flow of liquid metal in the particular steel making process for which the condition of the flow of the liquid metal is sought to be detected, such as the process shown and described in FIG. 1. The standard deviation is then preprogrammed into the signal processor 36 and applied to the calibration spectrum. This is subsequently compared with the data spectrum. The data spectrum is continuously generated and updated to measure the most up to date condition of the flow of liquid metal.

To determine the standard deviation to be applied to the calibration spectrum, the flow of the liquid metal is analyzed. The vibration sensor 30 is attached to the steel making equipment used in the steel making process to generate the sensor signal 44 in the manner described above. The raw signal 32 is then broken up into different frequency bands by the filter 40 of the signal processor 36 into a range between about 0.1 to 20 kHz. The intensity of each of these frequency bands is then measured and analyzed to determine which frequency bands respond to the flow conditions that are sought to be detected, e.g. slag entrainment. For flow conditions or events such as slag entrainment that generate low end noise, the lower end of the frequency band, between about 10 Hz–1 kHz, need only be considered.

Figure 3:
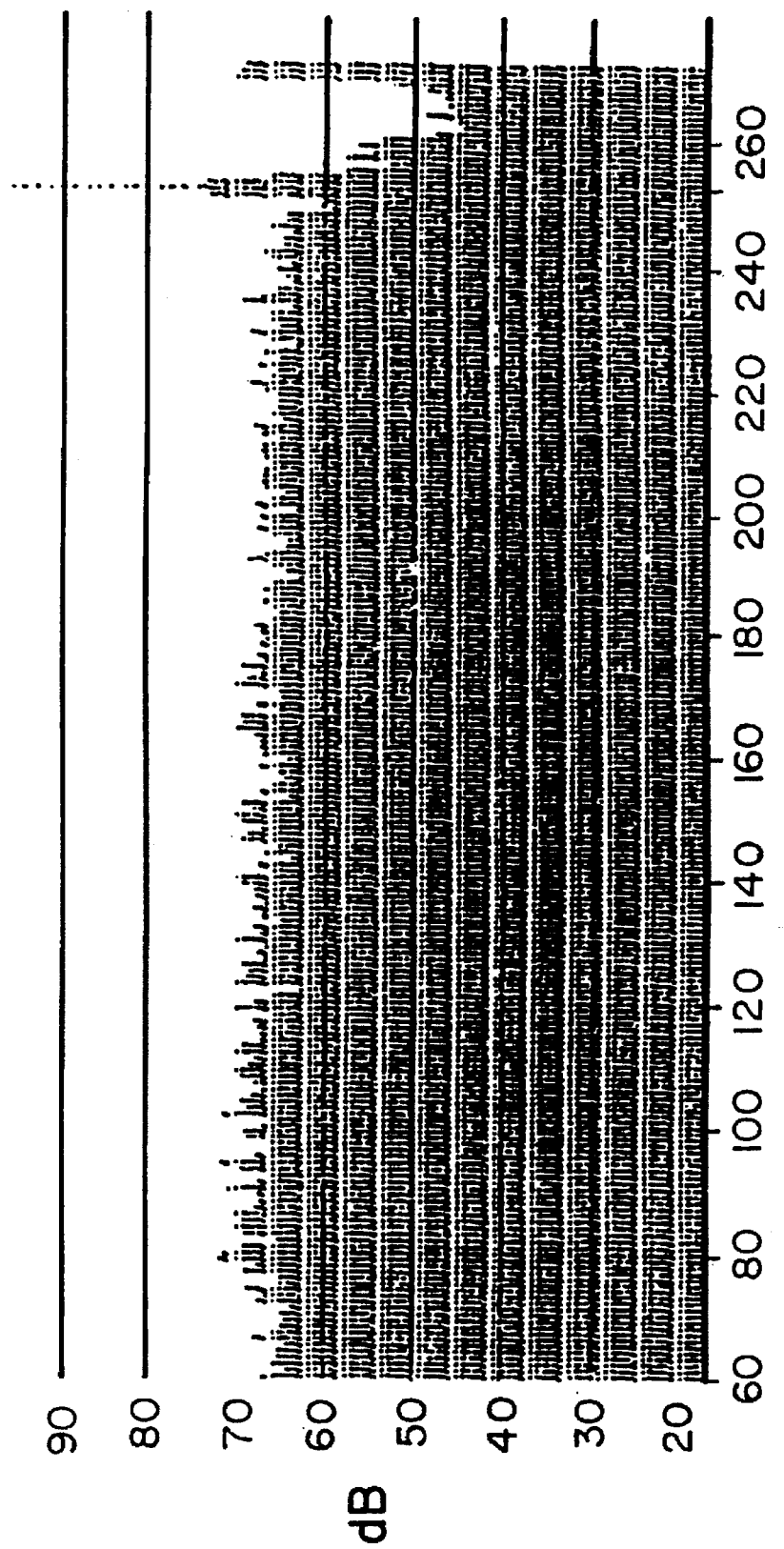
FIG. 3 is a graph representing a change in signal intensity at 40 Hz associated with an undesirable flow condition, such as slag entrainment or carryover.
Figure 4:
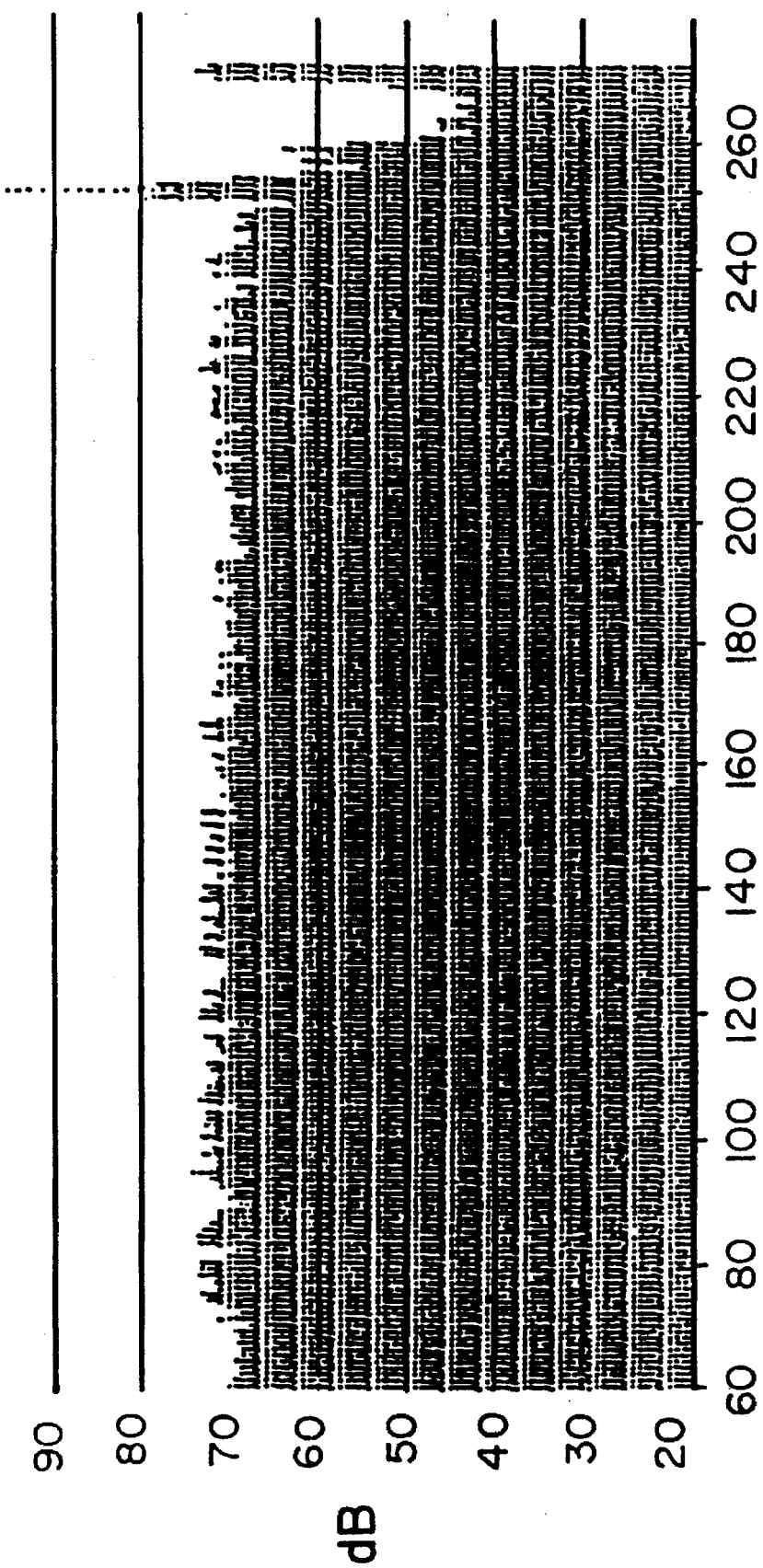
FIG. 4 is a graph representing a change in signal intensity at 50 Hz associated with an undesirable flow condition, such as slag entrainment or carryover.

Referring now to FIGS. 3, 4, two representative frequency bands are shown therein that have been generated for determining an exemplary standard deviation which may be applied to a calibration spectrum. FIG. 3 illustrates a 40 Hz signal and FIG. 4 illustrates a 50 Hz signal. The unit of the y-axis is dB and the unit of the x-axis is time. FIGS. 3, 4 were generated during a typical run of the method and apparatus of the present invention 28 in connection with a given steel making process such as the one shown and described at FIG. 1.

For the particular steel making process from which FIGS. 3, 4 were generated, the strong drop noted at the end of the graphs is associated with slag 26 passing through the ceramic tube 20 between the ladle 10 and the tundish 16. The intensity of the signal levels for both figures are fairly constant until the change in the flow of the liquid metal 12 associated with slag entrainment. The small spikes in FIGS. 3, 4 just before the large drop can be associated with vortexing within the tube 20 just before slag entrainment or carryover.

From FIGS. 3, 4 the frequency bands are determined to deviate in intensity approximately +5, −15 dB. In other words, in FIGS. 3, 4 the intensity level of an uncontaminated flow of liquid metal at 40 and 50 Hz, respectively, is approximately 70 dB. Once the flow of liquid metal is contaminated with slag or when some other undesirable flow condition occurs, the intensity of the frequency bands generated by the flow of the liquid metal deviates +5, −15 dB. It should be realized by those skilled in the art that while the analysis of only two frequency bands as set forth in FIGS. 3, 4 is described herein, all of the frequency bands within the range of 0.1 Hz–20 kHz should be analyzed, although the lower end of the frequency band, approximately between 10 Hz–1 kHz, need only be analyzed in a steel making process which typically generates low frequency noise, i.e., less than 1 kHz.

Once the standard deviation to be applied to the calibration spectrum is determined, it is programmed into the signal processor 36. The standard deviation can be increased or decreased to decrease or increase, respectively, the sensitivity of the method and apparatus 28. The apparatus 28 of the present invention is now ready to detect the condition of the flow of liquid metal in the desired steel making process, such as the one shown and described in FIG. 1

In a preferred embodiment, the method and apparatus 28 of the present invention is turned on when the amount of liquid steel 12 in the ladle 10 approaches approximately 20 tons to first generate the calibration spectrum to which the standard deviation is applied. A typical ladle used in a steel making process holds anywhere between 100–300 tons of liquid metal. At 15–20 tons of liquid metal 12 remaining in the ladle 10, the flow of the liquid metal 12 out of the ladle 10 is a substantially uncontaminated flow, although it should be realized by those skilled in the art that the apparatus 28 of the present invention can be turned on at any level of the liquid metal 12 in which the flow of liquid metal is not contaminated or in an undesirable condition to generate the calibration spectrum.

To generate the calibration spectrum, the vibration of the flow of the liquid metal 12 passing through the ceramic tube 20 is analyzed by the signal processor 36 in the manner described above for approximately three to fifteen seconds. This information is then fed into the comparator 42.

After the calibration spectrum is generated and fed into the comparator 42, the vibration of the flow of the liquid metal 12 passing through the ceramic tube 20 is analyzed by the signal processor 36 in the manner described above to generate the data spectrum. The comparator 42 of the signal processor 36 then compares the intensity of the frequency of vibration of the flow of liquid metal 12 traveling through the ceramic tube 20, i.e. the data spectrum, with the standard deviation applied to the calibration spectrum to generate the spectral comparison data 44 which is fed into the CPU 46. The data spectrum is constantly updated and compared with the standard deviation applied to the calibration spectrum to reflect the latest flow conditions.

The CPU 46 analyzes the spectral comparison data 44 to determine if the data spectrum is within the standard deviation applied to the calibration spectrum. If the spectral comparison data 44 determines that the data spectrum deviates outside the standard deviation applied to calibration spectrum, the CPU 46 is programmed to determine the extent of the deviation, e.g. how much the data spectrum deviates from the calibration spectrum, and for how long. If the deviation is determined by the CPU 46 to be acceptable, a positive status signal is passed to the operator signal panel 56. If the deviation is determined by the CPU 46 to be unacceptable, the status signal 54 declares an alarm state. This information is passed to the operator signal panel 56 to inform the operator of the signal panel 56 of the alarm state so that he can initiate closure of the valve 22, if appropriate. Alternatively, the status signal 54 in the alarm state can initiate automatic valve closure of the valve 22.

Once the valve 22 is closed, the ladle 10 is replaced with another ladle filled with liquid metal, not shown. When the amount of liquid metal contained in the second ladle approaches 15–20 tons, the method and apparatus 28 is again turned on and operated in the manner described above. A new calibration spectrum is generated and applied to the preprogrammed standard deviation and compared to a data spectrum in the manner described above. This is a continuous process.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for detecting the condition of the flow of liquid metal in or from a teeming vessel comprising:

a sensor for measuring a desired flow condition of liquid metal flowing from a teeming vessel to output a reference signal corresponding to the desired flow condition, and for monitoring the status of the flow condition of the liquid metal flowing from the teeming vessel to output a sensor signal corresponding to the status of the flow condition;

a signal processor for comparing the sensor signal to the reference signal and outputting a comparison signal; and a logic unit for receiving the comparison signal and for outputting a status signal indicative of the condition of the flow of the liquid metal in or from the teeming vessel.

2. The apparatus for detecting the condition of the flow of liquid metal of claim 1, wherein the sensor signal is received by a differential charge amplifier for eliminating low frequency noise before the sensor signal is received by the signal processor.

3. The apparatus for detecting the condition of the flow of liquid metal of claim 1, wherein the teeming vessel includes a valve to regulate the flow of liquid metal from the teeming vessel.

4. The apparatus for detecting the condition of the flow of liquid metal of claim 3, wherein the valve is in fluid communication with a passageway for flowing the liquid metal from the teeming vessel to a receiving vessel.

5. The apparatus for detecting the condition of the flow of liquid metal of claim 4, wherein the passageway is in operative engagement with a lifting device constructed and arranged to move the passageway into and out of fluid communication with the receiving vessel.

6. The apparatus for detecting the condition of the flow of liquid metal of claim 5, including a control panel for receiving the status signal.

7. The apparatus for detecting the condition of the flow of liquid metal of claim 6, wherein the control panel includes means for closing the valve to stop the flow of liquid metal out of the teeming vessel if the status signal indicates an undesired flow condition of the liquid metal in or from the teeming vessel.

8. The apparatus for detecting the condition of the flow of liquid metal of claim 6, wherein the control panel includes means for displaying the condition of the flow of liquid metal in or from the teeming vessel in response to the status signal.

9. The apparatus for detecting the condition of the flow of liquid metal of claim 1, wherein the sensor is a microphone.

10. The apparatus for detecting the condition of the flow of liquid metal of claim 1, wherein the sensor is an accelerometer.

11. The apparatus for detecting the condition of the flow of liquid metal of claim 1, wherein the signal processor divides the sensor signal into frequency bands.

12. The apparatus for detecting the condition of the flow of liquid metal of claim 11, wherein the signal processor outputs the frequency bands as a data spectrum.

13. The apparatus for detecting the condition of the flow of liquid metal of claim 1, wherein the signal processor divides the sensor signal into a frequency range of about 0.1 Hz to 20 kHz.

14. The apparatus for detecting the condition of the flow of liquid metal of claim 1, wherein the logic unit is a central processing unit.

15. The apparatus for detecting the condition of the flow of liquid metal of claim 1, wherein the status signal is indicative of an undesirable flow condition of the liquid metal in or from the teeming vessel.

16. The apparatus for detecting the condition of the flow of liquid metal of claim 15, wherein the undesirable flow condition includes one of vortexing, flow rate irregularity, surface collapse, flow plugging or gaseous aspiration.

17. The apparatus for detecting the condition of the flow of liquid metal of claim 1, wherein the status signal is indicative of a desirable flow condition of the liquid metal in or from the teeming vessel.

18. The apparatus for detecting the condition of the flow of liquid metal of claim 15, wherein the undesirable flow condition is slag entrainment.

19. The apparatus for detecting the condition of the flow of liquid metal of claim 1, wherein the signal processor compares the sensor signal to the reference signal in real time.

20. The apparatus for detecting the condition of the flow of liquid metal of claim 1, wherein the signal processor divides the sensor signal into a first set of frequency bands and outputs the first set of frequency bands as a calibration spectrum, divides the reference signal into a second set of frequency bands and outputs the second set of frequency bands as a data spectrum, and compares the data spectrum to the calibration spectrum in real time.

21. The apparatus for detecting the condition of the flow of liquid metal of claim 1, wherein the sensor signal is outputted after the reference signal is outputted.

22. A method for detecting a condition of a liquid metal flow in or from a teeming vessel, the method comprising the steps of:

flowing liquid metal from a teeming vessel;

measuring a desired flow condition of the liquid metal flowing from the teeming vessel;

converting the desired flow condition to a reference signal;

monitoring the status of the flow condition of the liquid metal flowing from the teeming vessel;

converting the status of the flow condition to a sensor signal;

comparing the sensor signal to the reference signal to output a comparison signal; and outputting a status signal in response to the comparison signal, the status signal being indicative of a condition of the flow of the liquid metal in or from the teeming vessel.

23. The method for detecting the condition of the flow of liquid metal of claim 22, wherein the sensor signal is amplified for eliminating low frequency noise before the sensor signal is compared to the reference signal.

24. A method for detecting a condition of a liquid metal flow in or from a teeming vessel, the method comprising the steps of:

flowing liquid metal from a teeming vessel;

measuring a desired flow condition of the liquid metal flowing from the teeming vessel;

monitoring the status of the flow condition of the liquid metal flowing from the teeming vessel;

comparing the desired flow condition to the status of the flow condition; and outputting a status signal indicative of a condition of the flow of the liquid metal in or from the teeming vessel.

25. An apparatus for detecting a condition of the flow of liquid metal in or from a teeming vessel comprising:

means for flowing liquid metal from a teeming vessel;

means for measuring a desired flow condition of the liquid metal flowing from the teeming vessel;

means for converting the desired flow condition to a reference signal;

means for monitoring the status of the flow condition of the liquid metal flowing from the teeming vessel;

means for converting the status of the flow condition to a sensor signal;

means for comparing the sensor signal to the reference signal to output a comparison signal; and means for outputting a status signal in response to the comparison signal, the status signal being indicative of a condition of the flow of the liquid metal in or from the teeming vessel.

26. An apparatus for detecting a condition of the flow of liquid metal in or from a teeming vessel comprising:

a sensor for measuring a desired flow condition of liquid metal flowing from the teeming vessel, and for monitoring the status of the flow condition of the liquid metal flowing from the teeming vessel;

a signal processor for converting the desired flow condition to a reference signal, for converting the status of the flow condition to a sensor signal, and for comparing the sensor signal to the reference signal to output a comparison signal; and a logic unit for outputting a status signal in response to the comparison signal to indicate a condition of the flow of the liquid metal in or from the teeming vessel.

27. The apparatus for detecting the condition of the flow of liquid metal of claim 1, wherein the signal processor divides the reference signal into frequency bands.

28. The apparatus for detecting the condition of the flow of liquid metal of claim 27, wherein the signal processor outputs the frequency bands as a calibration spectrum.

* * * * *